US008545761B2

(12) United States Patent
Cox

(10) Patent No.: US 8,545,761 B2
(45) Date of Patent: Oct. 1, 2013

(54) CHEMICAL AND BIOLOGICAL SENSOR

(75) Inventor: Donald P. Cox, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 209 days.

(21) Appl. No.: 12/731,658

(22) Filed: Mar. 25, 2010

(65) Prior Publication Data

US 2011/0236267 A1 Sep. 29, 2011

(51) Int. Cl.
*G01N 15/06* (2006.01)
(52) U.S. Cl.
USPC .............. 422/83; 422/88; 422/168; 422/68.1; 436/174; 340/540; 73/31.05

(58) Field of Classification Search
None
See application file for complete search history.

(56) References Cited

U.S. PATENT DOCUMENTS 4,198,208 A * 4/1980 Lerner et al. .................. 436/159
5,532,493 A 7/1996 Hale et al. .................. 250/458.1
5,744,902 A 4/1998 Vig .............................. 310/360
5,766,956 A 6/1998 Groger et al. ................. 436/164
5,807,758 A 9/1998 Lee et al. ...................... 436/526
5,866,430 A * 2/1999 Grow ................................ 506/6
6,067,842 A * 5/2000 Gygax et al. ................. 73/23.34
6,277,651 B1 8/2001 Groger et al. ................. 436/518
6,455,004 B1 9/2002 Tiefenthaler .................... 422/91
6,730,212 B1 5/2004 Yamagishi et al. ........ 205/777.5
6,933,164 B2 8/2005 Kubena ........................... 438/49
6,985,818 B1 1/2006 Samuels ......................... 702/22
7,087,434 B2 * 8/2006 Chen et al. .................... 436/130
7,096,125 B2 8/2006 Padmanabhan et al. ........ 702/24
7,129,096 B2 10/2006 Chilkoti et al. ............... 436/518
7,171,312 B2 1/2007 Steinthal et al. ................ 702/32
7,232,511 B1 6/2007 Venkatasetty ............ 204/403.01
7,249,859 B1 7/2007 Ptasinski et al. .............. 359/529
7,295,308 B1 11/2007 Samuels ....................... 356/326
7,368,294 B2 5/2008 Nikitin et al. ................. 436/518
7,500,379 B2 3/2009 Hines ........................... 73/24.06
7,542,884 B2 6/2009 Boris et al. ........................ 703/2
7,649,359 B2 1/2010 Prelas et al. .................. 324/452
7,708,413 B1 5/2010 Ptasinski et al. .............. 359/529
7,713,751 B2 5/2010 Nikitin et al. ................. 436/518
7,718,422 B2 5/2010 Chaton et al. ............. 435/288.7
8,038,952 B2 * 10/2011 Swanson ....................... 422/168
2002/0142477 A1 10/2002 Lewis et al. ................... 436/151
2002/0167003 A1 11/2002 Campbell et al. ............... 257/40
2002/0192653 A1 12/2002 Stetter et al. ...................... 435/6
2003/0114986 A1 6/2003 Padmanabhan et al. .......... 702/1

(Continued)

OTHER PUBLICATIONS

International Searh Report and Written Opinion; PCT/US2011/028023; pp. 11, Jul. 6, 2011.

*Primary Examiner* — Sally Merkling
(74) *Attorney, Agent, or Firm* — Lando & Anastasi, LLP

(57) ABSTRACT

The present disclosure provides a sensor device. The sensor device may include an intake port for an air sample connected to a mixing chamber. The mixing chamber may contain at least one device for the introduction of a liquid or gel detection improvement agent, or at least one mechanical dispersal device for the introduction of a solid detection improvement agent. The detection improvement agent may be operable to interact with a chemical or biological agent in the air sample. The mixing chamber may also include at least one heating or cooling plate and at least device for the introduction of water or an aromatic solvent into the air sample as well as at least one detection element able to detect a chemical or biological agent in the air sample. The mixing chamber may be connected to an exhaust port.

11 Claims, 1 Drawing Sheet

(56) References Cited

U.S. PATENT DOCUMENTS

| | | | |
|---|---|---|---|
| 2003/0198960 A1 | 10/2003 | Fan et al. | 435/6 |
| 2004/0023236 A1 | 2/2004 | Potter et al. | 435/6 |
| 2004/0099066 A1 | 5/2004 | Fries et al. | 73/863.21 |
| 2005/0133697 A1 | 6/2005 | Potyrailo et al. | 250/216 |
| 2005/0155410 A1 | 7/2005 | Manoosingh | 73/31.01 |
| 2006/0068490 A1 | 3/2006 | Tang et al. | 435/287.2 |
| 2006/0257956 A1 | 11/2006 | Basset et al. | 435/7.32 |
| 2007/0093970 A1 | 4/2007 | Padmanabhan et al. | 702/23 |
| 2008/0094051 A1 | 4/2008 | Williams et al. | 324/76.11 |
| 2009/0150090 A1 | 6/2009 | Brodsky | 702/31 |
| 2010/0039126 A1 | 2/2010 | Chen et al. | 324/693 |
| 2010/0167412 A1 | 7/2010 | Xiao et al. | 436/171 |
| 2010/0178207 A1 | 7/2010 | Nikitin et al. | 422/82.05 |
| 2010/0229658 A1 | 9/2010 | Glezer et al. | 73/863.81 |

* cited by examiner

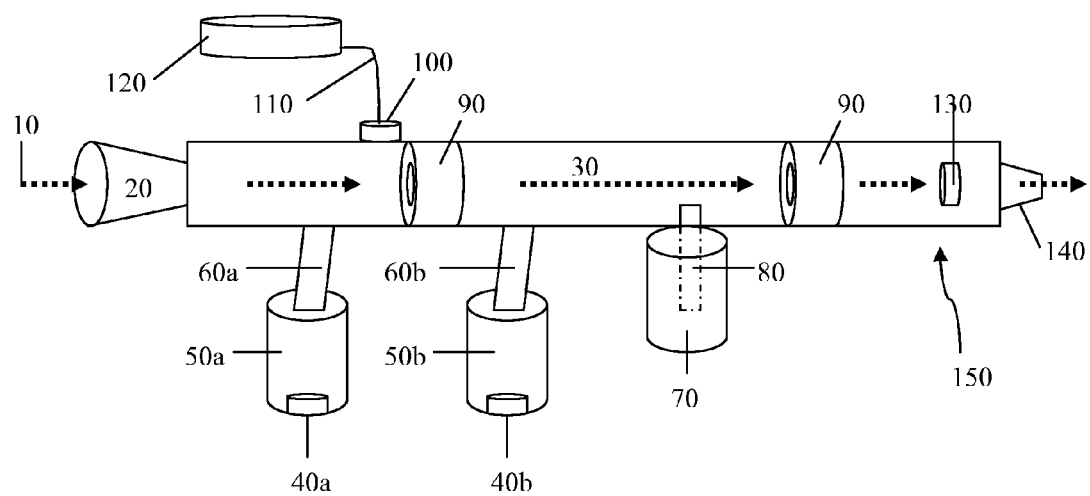

CHEMICAL AND BIOLOGICAL SENSOR

TECHNICAL FIELD

The current disclosure relates to a sensor able to detect chemicals or biological agents. According to one embodiment, the sensor may mimic a mammalian olfactory organ. According to another embodiment, the sensor may further detect the effects of neutralization agents on the chemicals or biological agents.

BACKGROUND

Sensors able to detect chemical or biological agents often contain polymer or biometric films as the sensing mechanism. Such sensors often fail to detect many native chemicals or biological agents, such as may be found in ambient air samples. In many cases, modification of a native chemical or biological agent as found in ambient air is required in order for the sensor to be able to detect it. In other cases, other ambient air conditions, such as temperature or humidity interfere with detection. In still other cases, low reactivity of the film, particularly under ambient conditions, may interfere with detection.

In addition to their inability to detect chemical or biological agents in air, many sensors are also unable to detect the effectiveness of any neutralization agents on these chemical or biological agents.

Attempts to overcome these deficiencies in current systems have tended to focus on changes to the polymer or biometric films rather than on other properties that may affect detection.

SUMMARY

Accordingly, the present disclosure provides, in one embodiment, a sensor device for the detection of a chemical or biological agent. The sensor device may include an intake port for an air sample connected to a mixing chamber. The mixing chamber may contain at least one storage container, connection tube, and atomizer for the introduction of a liquid or gel detection improvement agent, or at least one mechanical dispersal device for the introduction of a solid detection improvement agent. The detection improvement agent may be operable to interact with a chemical or biological agent in the air sample. The mixing chamber may also include at least one heating or cooling plate and at least one storage container and wick for the introduction of water or an aromatic solvent into the air sample as well as at least one detection element able to detect a chemical or biological agent in the air sample. The detection element may include a polymer film, a biometric film, or olfactory cells. The polymer film, or biometric film may be arranged in an array of films, each of which may be sensitive to a different chemical agent. The mixing chamber may be connected to an exhaust port.

According to a second embodiment, the disclosure provides a sensor device for the detection of a chemical or biological agent. The sensor device may include an intake port for an air sample connected to a mixing chamber. The mixing chamber may contain at least one means for the introduction of a detection improvement agent. The detection improvement agent may be operable to interact with a chemical or biological agent in the air sample. The mixing chamber may also include at least one heating or cooling means and at least one means for the introduction of water or an aromatic solvent into the air sample as well as at least one detection element able to detect a chemical or biological agent in the air sample. The detection element may include a polymer film, a biometric film, or olfactory cells. The polymer film, or biometric film may be arranged in an array of films, each of which may be sensitive to a different chemical agent. The mixing chamber may be connected to an exhaust port.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIG. 1 illustrates a chemical and biological sensor according to an embodiment of the present disclosure.

DETAILED DESCRIPTION

The current disclosure relates to a sensor able to detect chemicals or biological agents. According to a further embodiment, the sensor may mimic a mammalian olfactory organ.

According to another embodiment, the sensor may amplify the sensitivity to an agent as compared to film-based sensors with the same film, but lacking one or more detection improvement features disclosed herein. Such detection improvement features may include, but are not limited to, adding one or more amplifying agents to the air sample, adding one or more atomized agents to the air sample, and adjusting the sample temperature.

According to another embodiment, the sensor may further be able to detect the effects of neutralization agents on the chemicals or biological agents. In such an embodiment, the neutralization agent may be introduced to the sample alone or in combination with the detection improvement features.

One embodiment of the invention, described in FIG. 1, air sample 10 is introduced into sensor device 150 through intake port 20. The sensor device may include any type of sensor device, including a handheld device, a fixed device such as an airport screening station or a vehicle-mounted device, or a laboratory device. Air sample 10 may be any gaseous sample, including, ambient air and exhaust air from an air collection or sampling device (not shown), such as a device integral in an HVAC system. According to particular embodiments, air sample 10 may be a continuous flow of gaseous sample, or it may be a representative sample which may be held in sensor device 150 during processing and testing.

Air sample 10 may then enter mixing chamber 30, in which one or more detection improvement features may be implemented.

According to one embodiment, a detection improvement agent may be added to the air sample 10. Example detection improvement agents may include a protein, a lipid, or another chemical agent able to interact, such as, by a chemical reaction, with a biological or chemical agent in the air sample 10. The detection improvement agent may generally improve the ability of detection element 130 to detect the biological or chemical agent in air sample 10, or to detect its neutralization. The exact detection improvement agent employed may be determined by the nature of the chemical or biological agent to be detected. In one embodiment the detection agent may include agents commonly used to detect the chemical or biological agent in other laboratory or assessment procedures.

Detection improvement features similar to those described above for the introduction of detection improvement agents may also be used to introduce one or more neutralization agents into air sample 10. The particular neutralization agents selected may include agents commonly used to neutralize the detected chemical or biological agent in other laboratory or assessment procedures.

In specific embodiments, the detection improvement agent may be in the form of a solid, a liquid, or a gel. The physical and chemical properties of the detection improvement agent may determine how it is introduced into mixing chamber 30. For example, according to one embodiment, solid agents may be introduced by mechanical dispersal. According to another embodiment, gel or liquid agents may be introduced by mechanical atomization or evaporation.

According to one specific embodiment, one or more liquid or gel detection improvement agents may be placed in a storage container 40a. Storage container 50a may also include an atomizer 40a, such as an ultrasonic or radio frequency atomizer. The storage container may be connected to mixing chamber 30 by connective tube 60a. During operation of sensor device 150, atomizer 40a may atomize a liquid or gel detection improvement agent located in storage container 50a. The atomized agent may then travel via connective tube 60a to mixing chamber 30, where it may interact with air sample 10 to improve detection of a chemical or biological agent in air sample 10.

According to another specific embodiment, one or more liquid or gel detection improvement agents may be placed in storage container 120. The liquid or gel detection agent may travel via connective tube 110 through atomizer 100, such as an ultrasonic or radio frequency atomizer, into mixing chamber 30. This system may be used to atomize the agent closer to the mixing chamber than the prior embodiment in which atomization occurs in storage container 50a.

According to another specific embodiment, the temperature of air sample 10 may be adjusted using a baffle of heating or cooling plates 90, or an alternative heating or cooling apparatus (not shown). Heating or cooling plates, according to one embodiment, may include a Peltier Diode heat transfer plates. According to another embodiment, they may be connected to an external heating or cooling device. Multiple heating or cooling plates may be included in sensor device 150, or only one set may be included. Heating or cooling plates may be placed before or after other detection improvement features, such as features for the introduction of detection improvement agents, to optimize the temperature of air sample 10 for interaction of chemical or biological agents therein with the detection improvement agents. Heating or cooling plates may be further placed prior to detection element 130 (as shown in FIG. 1) to adjust the temperature of air sample 10 to improve detection of a chemical or biological agent by detection element 130 or detection of neutralization of a chemical or biological agent by detection element 130.

According to another specific embodiment, the humidity of air stream 10 may be adjusted to facilitate interaction of a detection improvement agent and a chemical or biological agent in air stream 10 or to improve detection of a chemical or biological agent by detection element 130 or detection of neutralization of a chemical or biological agent by detection element 130. According to one embodiment, water in storage container 70 may enter mixing chamber 30 via a wick 80, such as a fibrous wick. According to other embodiments, other detection improvement agents that are evaporable in air stream 10, such as aromatic solvents, may also be provided in storage container 70 and may enter air stream 10 via evaporation from wick 80.

According to the embodiment shown in FIG. 1, after passing the detection improvement features, air stream 10 reaches detection element 130. According to a specific embodiment, detection element 130 may include a film, such as a polymer or biometric film. According to another specific embodiment, detection element 130 may include an array of polymer or biometric films, each film being sensitive to a specific chemical or biological agent. The polymer film, or biometric films may be arranged in an array of films, each of which may be sensitive to a different chemical agent. According to another specific embodiment, detection element 130 may include an array of olfactory cells. After detection via the film, air stream 10 leaves sensor device 150 via exhaust port 140.

Sensor device 150 may contain multiples of various detection improvement features. For example, as shown in FIG. 1, an additional storage container 50b, atomizer 40b, and connective tube 60b may be included to provide a different detection improvement agent to mixing chamber 30.

One or more detection elements 130 may also be included in mixing chamber 30, or may be in a separate compartment of sensor device 150 (not shown). Further, one or more mixing chambers 30 may be included in sensor device 150 (not shown). In embodiments containing multiple mixing chambers, each chamber 30 may include a detection element 130, or some chambers may have detection elements while others do not. For example, it may be advantageous to implement certain detection improvement features in a separate chamber from the detection element, particularly if the detection improvement feature may improve detectability of an agent in the sample overall, but have a negative effect on the detection element, for example due to an unsuitable temperature or an undesirable chemical reaction with the detection element.

One or more filters (not shown) may be present before or between multiple mixing chambers 30 or before single mixing chamber 30 to remove certain materials already present in the air sample or added as a detection improvement feature that may have a negative effect on the detection element. Such filters may be designed to minimize or avoid removal of the chemical or biological agent or derivative thereof to be detected by a detection element 130.

According to one embodiment, multiple stages of air sample collection, implementation of a detection improvement feature, and detection may be established in parallel or in series. For example, the air sample 10 may be presented to one or more detection elements 130 simultaneously, or one after another. Detection improvement features may be introduced at various stages. Selection of detection improvement features and their arrangement with detection elements in various stages or using separate mixing chambers 30 may allow more complete characterization of a chemical or biological agent in air sample 10 than if a single stage or single detection element 130 sensor were used. According to a specific embodiment, these stages may be arranged to mimic the steps of laboratory sample preparation and analysis.

According to another embodiment, a neutralization agent may be introduced in at least one mixing chamber 30 to determine if the neutralization agent is affective against any chemical or biological agent in air sample 10. The neutralization agent may be introduced in combination with or followed by one or more detection improvement features. In one embodiment, mixing chambers 30 and detection elements 130 may be arranged in series so that first the agent is detected and then the effects of the neutralization agent are detected. In another embodiment, mixing chambers 30 and detection elements 130 may be arranged in parallel, so that air sample 10 enters multiple mixing chambers 30, at least one of which is designed to detect and identify the chemical or biological agent, and at least another of which is designed to determine the effects of at least one neutralization agent. These detection events may occur substantially simultaneously due to the parallel nature of the mixing chambers 30.

According to specific embodiments, sensor device 150 may generally mimic a mammalian olfactory organ. For example, the temperature and humidity of air stream may be adjusted to close to that found in a mammalian olfactory organ, such as 90-95% humidity.

The invention claimed is:

1. A sensor device for the detection of a chemical or biological agent comprising:
- an intake port for an air sample;
- a mixing chamber connected to the intake port, the mixing chamber containing:
  - at least one storage container, connection tube, and atomizer comprising a liquid or gel detection improvement agent, or at least one mechanical dispersal device comprising a solid detection improvement agent, the at least one of the liquid or gel detection improvement agent and solid detection improvement agent operable to interact with a chemical or biological agent in the air sample, the at least one storage container, connection tube, and atomizer, or at least one mechanical dispersal device connected directly downstream of the intake port and upstream of at least one heating or cooling plate;
  - at least one storage container and wick for the introduction of water or an aromatic solvent into the air sample connected downstream of the at least one storage container, connection tube, and atomizer, or at least one mechanical dispersal device; and
  - at least one detection element selected from the group consisting of a polymer film, a biometric film, or olfactory cells, and an array of polymer or biometric films, each sensitive to a different chemical or biological agent operable to detect a chemical or biological agent in the air sample, the at least one detection element positioned downstream of the at least one storage container and wick; and
- an exhaust port positioned downstream of the at least one detection element.

2. The sensor device of claim 1, wherein the atomizer comprises an ultrasonic or radio frequency atomizer.

3. The sensor device of claim 1, wherein the at least one of the liquid and gel detection improvement agent and solid detection improvement agent comprises a protein.

4. The sensor device of claim 1, wherein the at least one of the liquid and gel detection improvement agent and solid detection improvement agent comprises a lipid.

5. The sensor device of claim 1, wherein the at least one of the liquid and gel detection improvement agent and solid detection improvement agent chemically reacts with the chemical or biological agent.

6. The sensor device of claim 1, wherein the detection element detects the chemical or biological agent by detection of a product of an interaction of the chemical or biological agent with the detection improvement agent.

7. The sensor device of claim 1, further comprising at least one storage container and connection tube operable to introduce a neutralization agent into the air sample.

8. The sensor device of claim 7, further comprising a detection element operable to detect the neutralization of the chemical or biological agent by the neutralization agent.

9. The sensor device of claim 1, further comprising at least one additional mixing chamber, wherein the mixing chambers are placed in series.

10. The sensor device of claim 1, further comprising at least one additional mixing chamber, wherein the mixing chambers are placed in parallel.

11. The sensor device of claim 1, wherein the heating or cooling plate comprises a Peltier Diode heat transfer plate.

* * * * *